United States Patent

Brennen et al.

[11] Patent Number: 5,336,254
[45] Date of Patent: Aug. 9, 1994

[54] DEFIBRILLATION LEAD EMPLOYING ELECTRODES FABRICATED FROM WOVEN CARBON FIBERS

[75] Inventors: Kenneth R. Brennen, Fridley; Terrell M. Williams, Coon Rapids; Robert A. Gabler, Fridley, all of Minn.

[73] Assignee: Medtronic, Inc., Minneapolis, Minn.

[21] Appl. No.: 950,533

[22] Filed: Sep. 23, 1992

[51] Int. Cl.⁵ ............................................. A61N 1/05
[52] U.S. Cl. ............................................. 607/129
[58] Field of Search ............................ 128/784–786, 128/798, 419 P, 419 D; 607/116, 122, 129, 5

[56] References Cited

U.S. PATENT DOCUMENTS

| | | | |
|---|---|---|---|
| 4,161,952 | 7/1979 | Kinney et al. | 128/786 |
| 4,248,237 | 2/1981 | Kenny | 128/419 P |
| 4,291,707 | 9/1981 | Heilman et al. | 128/784 |
| 4,325,389 | 4/1982 | Gold | 128/784 |
| 4,817,634 | 4/1989 | Holleman et al. | 128/784 |
| 4,938,231 | 7/1990 | Milijasevic et al. | 128/784 |
| 4,971,070 | 11/1990 | Holleman et al. | 128/784 |
| 5,005,587 | 4/1991 | Scott | 128/786 |
| 5,016,645 | 5/1991 | Williams et al. | 128/784 |
| 5,105,826 | 4/1992 | Smits et al. | 128/784 |
| 5,143,089 | 9/1992 | Alt | 128/784 |

FOREIGN PATENT DOCUMENTS

| | | | |
|---|---|---|---|
| 1357022 | 12/1987 | U.S.S.R. | 128/784 |
| 1219017 | 1/1971 | United Kingdom . | |

*Primary Examiner*—Lee S. Cohen
*Attorney, Agent, or Firm*—Reed A. Duthler; Harold R. Patton

[57] ABSTRACT

An implantable cardioversion or defibrillation lead provided with a large surface, carbon fiber electrode. The lead takes the form of an elongated tubular braid of carbon fiber, provided with a central core of insulating plastic. Over the majority of the braid's length, it is covered by an outer sheath of insulating plastic as well, serving as a lead conductor. At its distal end, the braid is not covered, and the exposed portion of the braid serves as the electrode.

5 Claims, 4 Drawing Sheets

DEFIBRILLATION LEAD EMPLOYING ELECTRODES FABRICATED FROM WOVEN CARBON FIBERS

BACKGROUND OF THE INVENTION

The present invention is directed toward implantable stimulation electrodes generally, and more particularly to implantable defibrillation electrodes of the types typically used with implantable automatic defibrillators.

Commercially available implantable defibrillation leads typically employ metal electrodes for delivery of defibrillation pulses. In the context of epicardial and subcutaneous leads, the electrode typically takes the form of a mesh of woven metal. A typical electrode of this type is illustrated in U.S. Pat. No. 4,291,707, issued to Heilman et al. In the context of endocardial electrodes, defibrillation electrodes typically take the form of an elongated wire coil, mounted to an insulative lead body of silicone rubber or other material. A typical endocardial defibrillation lead is illustrated in U.S. Pat. No. 4,161,952, issued to Kinney et al.

Implantable defibrillators in clinical investigation, manufactured by Medtronic, Inc., employ subcutaneous and epicardial electrodes in which the metal mesh disclosed in the above electrodes has been replaced by one or more elongated electrode coils mounted to an insulative backing. Electrodes corresponding to those currently in clinical investigation are illustrated in U.S. Pat. No. 4,817,634, issued to Holleman et al, incorporated herein by reference in its entirety. Epicardial and subcutaneous defibrillation electrodes employing elongated electrode coils, but lacking an insulative backing member are disclosed in allowed U.S. patent application Ser. No. 07/604,686 now U.S. Pat. No. 5,105,826 by Smits.

Over the years, the patent art related to implantable defibrillation leads has included a number of references which suggest the use of carbon fibers as a substitute for the wire mesh and conductor coils of epicardial and subcutaneous electrode leads, as disclosed in the patents cited above. References suggesting this substitution include German Patent Application DE 3914662 by Alt and U.S. Pat. No. 4,938,231, issued to Milijasevic et al. Similarly, the use of carbon fibers as conductors or electrodes for pacing leads has also been suggested, for example in U.S. Pat. No. 4,325,389 issued to Gold, and British Patent No. 121017, issued to Thompson Medical Telco.

As a practical matter, the recommendations to incorporate carbon fibers set forth in the patents cited above has not been followed in the context of defibrillation leads. A primary reason is the fact that these leads must deliver extremely high energy pulses. For this reason, commercial embodiments have typically employed metals of extremely low resistivity, such as drawn brazed strand wire for use as a conductor in the lead body and platinum for use as an electrode surface. The problems associated with the use of carbon both to carry the high energy pulses through the lead and to deliver them to the tissue have been addressed to some extent in the above-cited Alt application, in which the use of isotropic carbon is encouraged, as opposed to more typical anisotropic carbon fibers. The use of isotropic carbon fibers is stated to reduce the contact resistance between the individual fibers and to be a benefit in the context of a defibrillation electrode, in that delivery of the current occurs more evenly along the length of the fiber, rather than being focused primarily at the end of the fiber.

SUMMARY OF THE INVENTION

The present invention addresses the notion of employing carbon fibers in a defibrillation lead in a fashion different from the prior art. Rather than attempting to optimize the conductive properties of the carbon to make them more suitable for use in this application, the present inventors have instead employed a newly available type of carbon fibers covered with a metal coating, in which the coating, rather than the fibers, constitutes the primary current carrier. In particular, the inventors have employed a commercially available carbon fiber provided with a thin coating of nickel, to which the inventors have added a platinum, gold or other inert metal overcoating deposited by sputtering or electrodeless deposition is added in order to enhance biocompatibility and further reduce resistivity.

The metal coating of the carbon fibers overcomes various practical problems associated with the use of carbon fibers in the context of defibrillation electrode leads. The fiber to fiber resistance is reduced to the contact resistance associated with the metal, and becomes insignificant. The metal, being the primary current carrier, is particularly well adapted to deliver the defibrillation pulse energy along its entire exposed length. While it is undoubtedly true that microscopic cracks or breaches will occur in the metal coating as a function of bending, weaving or other processing of the carbon fibers, the underlying carbon fiber will effectively bridge this gap. Due to the relatively short lengths of carbon fiber that will actually be involved in bridging gaps in the metal coating, the overall resistivity of the metallized fibers remains extraordinarily low. Conversely, the low contact resistance provided by the metal coating assists in dealing with breaks in the individual carbon fibers by making adjacent fibers more effective in bridging such breaks.

Beginning with the new type of carbon fibers, the inventors have attempted to optimize the structure of the defibrillation electrodes fabricated from the fibers. Rather than attempt to weave a patch electrode from the carbon fibers, as suggested in the above-cited Milijasavic patent, the inventors instead have employed metallized carbon fibers woven into a hollow, tubular braid. This hollow, tubular braid serves as the lead conductor, extending from the connector assembly at the proximal end of the lead to the electrode at the distal end of the lead. Where it serves as a lead conductor, the carbon braid is provided with an outer sheath of insulative material such as silicone rubber or polyurethane.

At the distal end of the lead, the carbon braid is exposed to the exterior of the lead for a substantial distance and is curved or branched to effectively provide a generally planar, large surface area patch electrode. The braid may follow a spiral or sigmoidal path, for example. Unlike the braided electrodes in the Alt patent, in the area in which the fiber is exposed for use as an electrode, it is provided with an internal core of silicone rubber, polyurethane or other biocompatible insulative material to reduce fibrotic ingrowth into the carbon fiber braid. In some embodiments, the carbon fiber braid is mounted to an insulative backing member. In other embodiments, the carbon fiber braid is simply mounted around a silicone or other plastic member which assumes a preformed configuration, and has no insulative backing member.

The use of the tubular hollow carbon fiber braid is particularly advantageous in that it allows for a continuous structure extending from the connector at the proximal end of the lead all the way through and including the electrode. There is no necessity for any transitional structures to connect the lead to the electrode, greatly simplifying construction of the lead.

DETAILED DESCRIPTION OF THE PREFERRED EMBODIMENTS

Figure 1:
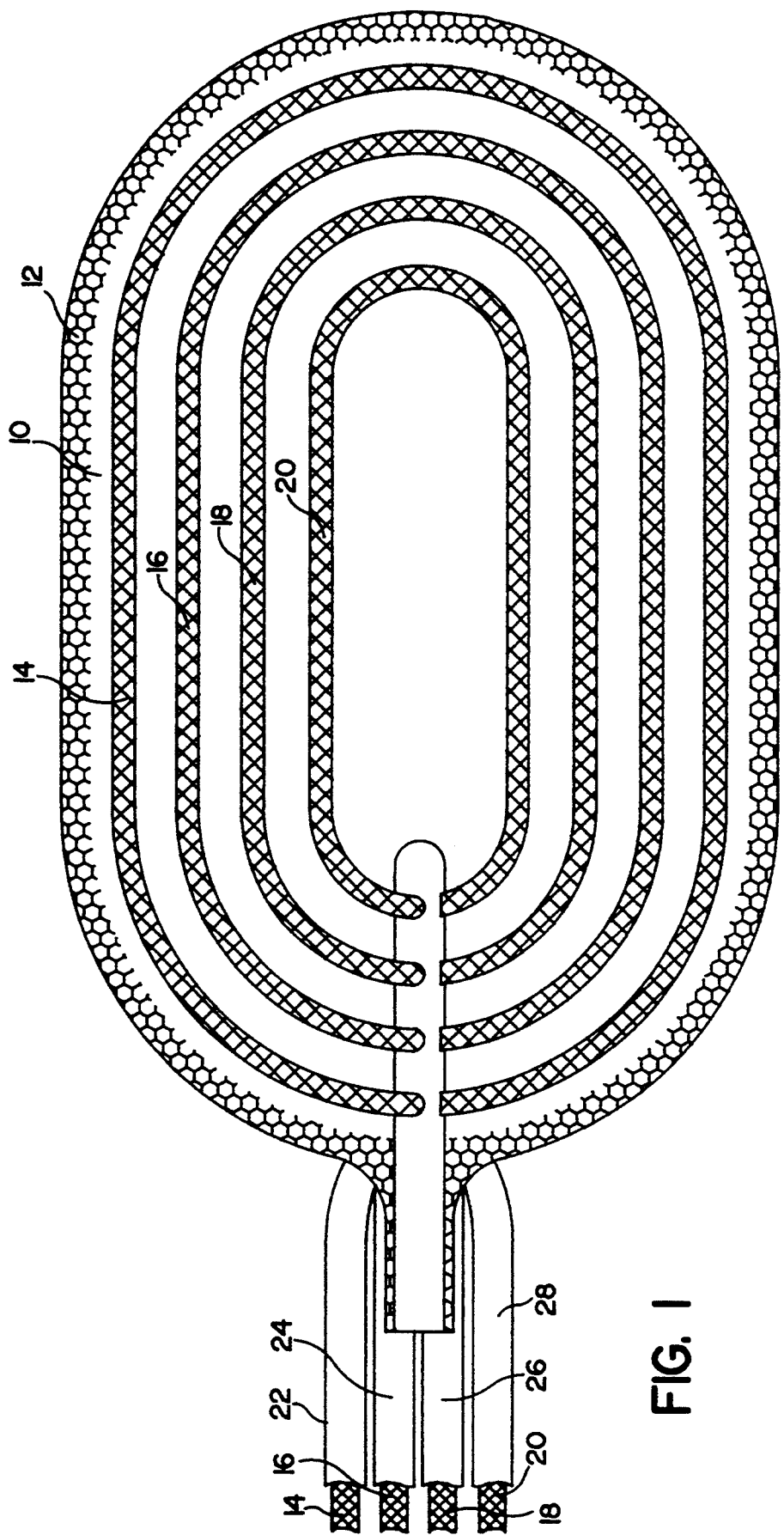
FIG. 1 is a bottom, plan view of a defibrillation electrode according to the present invention.

FIG. 1 shows a bottom, plan view of an electrode according to the present invention. The electrode is provided with an insulative electrode pad 10, corresponding to the electrode pad illustrated in the above-cited U.S. Pat. No. 4,817,634, issued to Holleman et al. incorporated herein by reference in its entirety. The pad 10 is a generally planar structure fabricated of silicone rubber, polyurethane or other flexible insulative biocompatible plastic. It is provided with a plurality of concentric, oval shaped grooves into which the braided carbon fiber electrodes are mounted.

The periphery of the electrode pad 10 is provided with a dacron reinforcement mesh 12, to assist in suturing the pad to the myocardium or to subcutaneous tissue, and to assist in preventing tearing of the pad. The dacron mesh, as illustrated, is limited to the external periphery of the electrode pad and does not extend into the area between the carbon fiber electrodes.

The lead of FIG. 1 is provided with four separate carbon fiber electrodes 14, 16, 18 and 20. Each of these electrodes takes the form of tubular braid of metallized carbon fibers, each laid in one of the oval shaped, concentric grooves in electrode pad 10. Each of the carbon fiber electrodes 14, 16, 18 and 20 is provided with an inner tubular core of silicone rubber, around which the tubular braid of carbon fibers is mounted. The carbon fibers are retained within the grooves in base pad 10 by means of medical adhesive, which bonds the tubular core within the carbon fiber braids to the pad 10.

Figure 5:
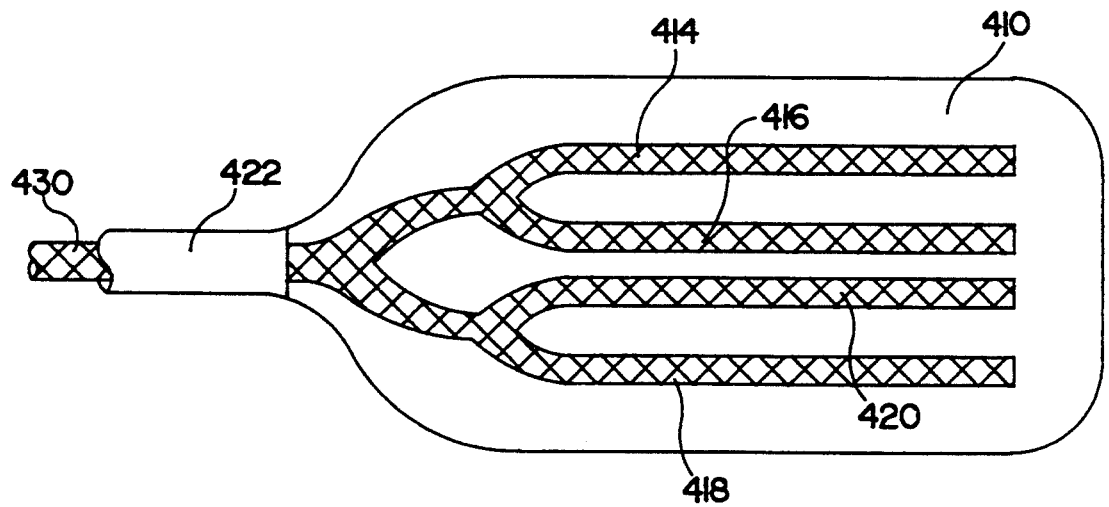
FIG. 5 is a bottom, plan view of an alternative embodiment of an electrode according to the present invention.

Each of the carbon fiber electrodes 14, 16, 18 and 20 exits the upper surface of the electrode pad at which point they are provided with tubular, insulative sheaths 22, 24, 26 and 28, which cover the carbon fiber braids until they reach the proximal end of the lead. In the embodiment illustrated in FIG. 1, each of the electrodes 14, 16, 18 and 20 may be provided with its own electrical connector. Alternatively, the carbon fiber electrodes may all be interconnected at the proximal end of the lead to a single connector or, may be interconnected by means of a manifold, weaving, conductive adhesive or other structure at the electrode pad. In particular, it is anticipated that by employing the weaving methods employed to fabricate bifurcated woven vascular grafts, a single large bore braid may be reduced to multiple, smaller bore carbon braids for producing a carbon fiber electrode. Such an alternative structure is illustrated in FIG. 5, below.

Figure 2:
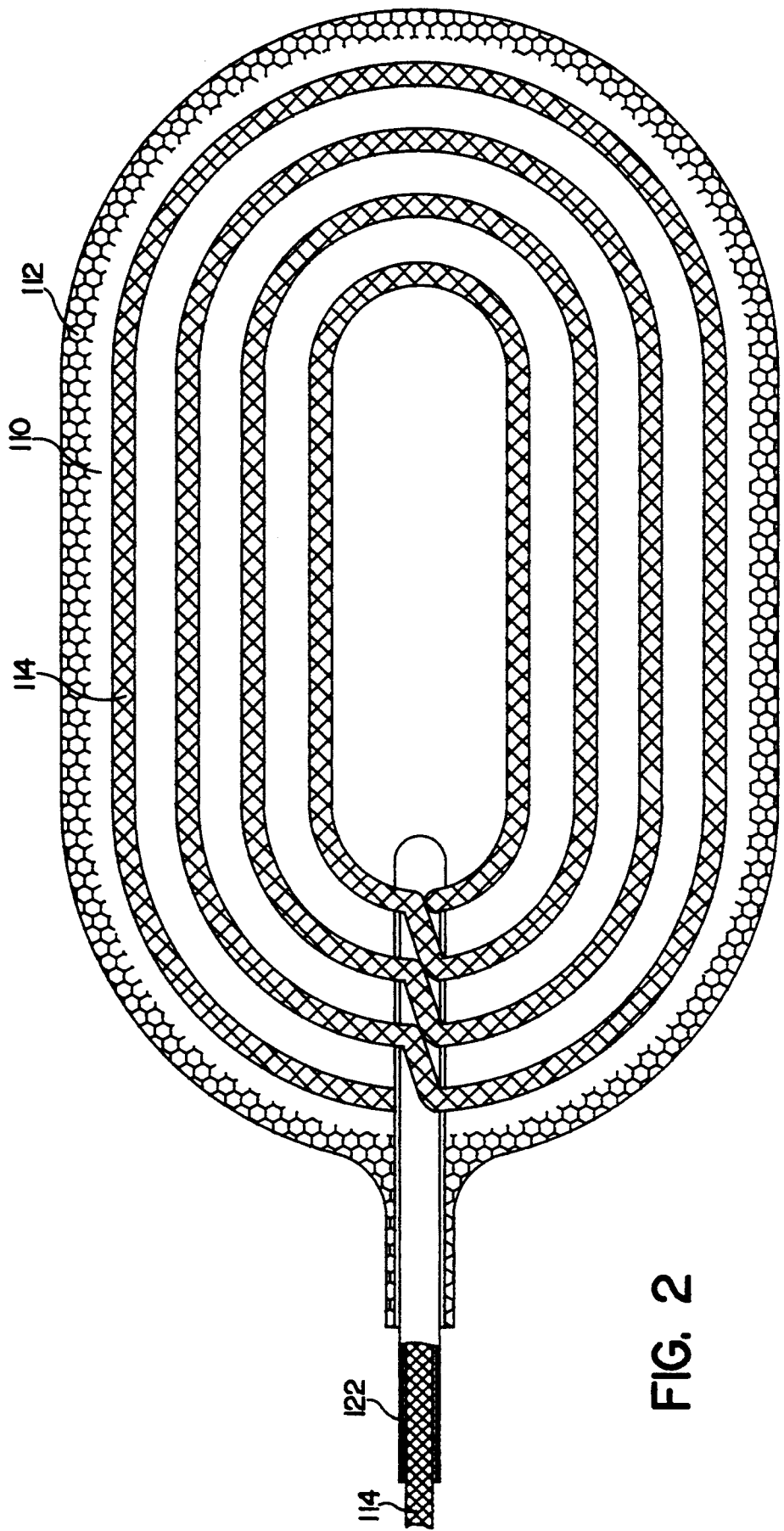
FIG. 2 is a bottom, plan view of a defibrillation electrode according to the present invention.

FIG. 2 is a diagram of an alternate embodiment of a lead employing the present invention. It too is provided with an electrode pad 110 which corresponds to pad 10 in FIG. 1. Pad 110 is similarly provided with a dacron enforcement mesh 112 around its external periphery. In the electrode FIG. 2, only one carbon fiber electrode 114 is provided, mounted to the grooves within pad 110 to provide a spiral shaped electrode. On exiting the electrode pad, electrode 114 is provided with a insulative sheath 112 which extends to the proximal end of the lead.

Figure 3:
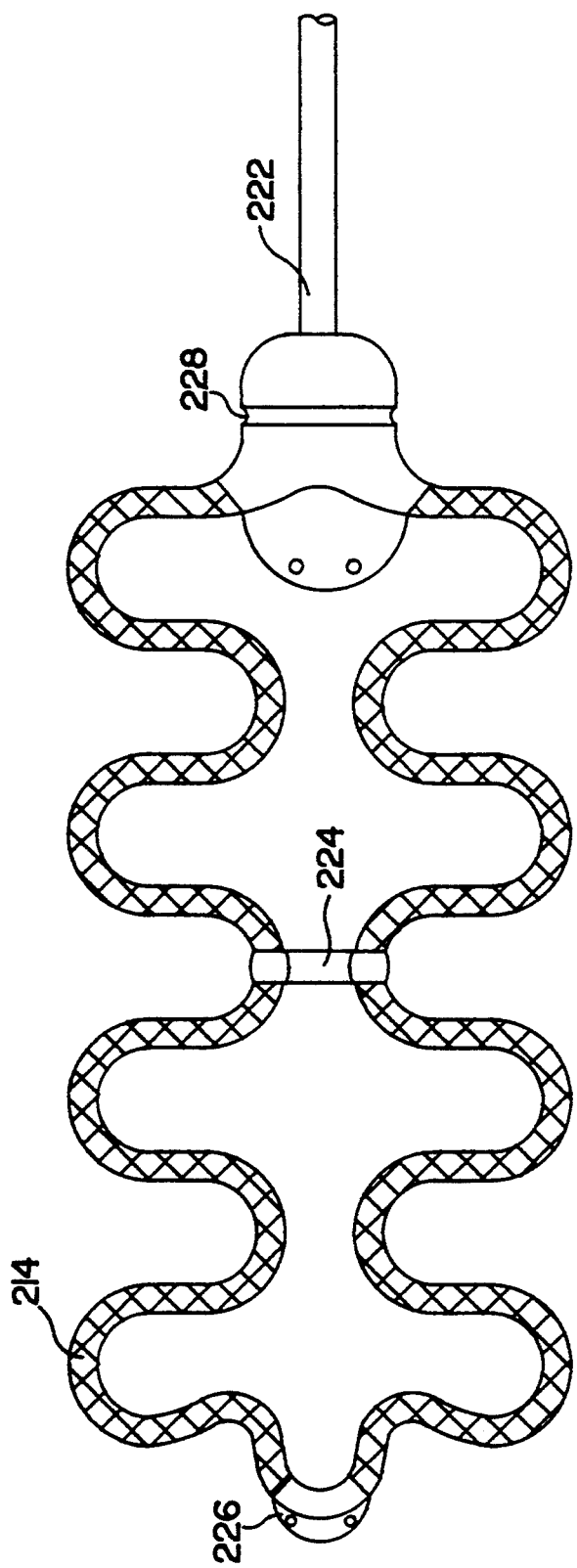
FIG. 3 is a top, plan view of the a defibrillation electrode according to the present invention.

FIG. 3 illustrates yet another alternative embodiment of a lead employing the present invention. In this embodiment, the carbon fiber electrode 214 is mounted to an insulative core which has performed or molded to follow a sigmoidal path. The configuration illustrated corresponds to that illustrated in the allowed U.S. patent application Ser. No. 07/604,686, of Smits et al., filed Oct. 26, 1990, and incorporated herein by reference in its entirety. It is believed that this embodiment of the invention retains all of the advantages discussed in the Smits application, associated with the sigmoidal configuration. In this case, only a single braided carbon fiber electrode 214 is provided, and it extends proximally within insulative sheath 222, until the proximal end of the lead. Assembly of the lead is accomplished by sliding the tubular carbon braid over the previously molded sigmoidal silicone rubber core, and subsequently molding the bridging member number 224, suture pad 226 and the transition member 228 over the carbon electrode. The suture pad 226, the bridging member 224 and the transition member 228 are all preferably fabricated of silicone rubber or other biocompatible, flexible insulative plastic and bond to the sinusoidal core through the interstices in the carbon braid.

Figure 4:
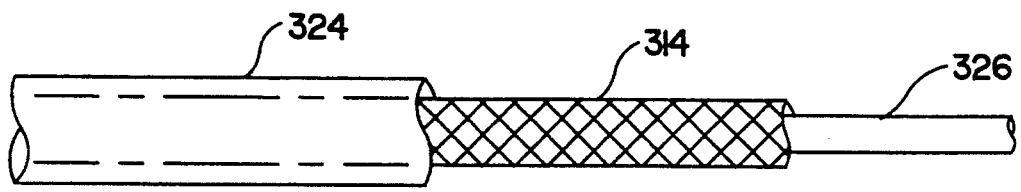
FIG. 4 is a cutaway view illustrating the interrelation of the carbon fiber braid, its exterior insulation and its interior core as used in the present invention.

FIG. 4 shows the basic structure of the carbon fiber electrode. A tubular braid 314 of metallized carbon fibers is shown extending from the distal end of an insulative sheath 324. That portion of the tubular carbon braid which extends within the insulative sheath 324 forms the lead conductor. Also illustrated is core 326, located within the carbon fiber 314.. This core may be tubular or solid and, in the case of electrodes as in FIG. 3, may be provided with an internal wire or other reinforcement. The core may simply follow the path of the carbon fibers, as mounted to a base pad, as illustrated in FIGS. 1 and 2 or may itself impart a curved configuration to the carbon fiber electrode as illustrated in FIG. 3. The core may extend the length of the braid 314 or may be limited to that portion of the braid exposed to the exterior of sheath 322.

FIG. 5 is an illustration of yet another embodiment of an electrode according to the present invention, in which the weaving techniques employed to produce bifurcated tubular structures in the context vascular grafts have been applied to the context of implantable defibrillation leads. As illustrated, a single, large diameter tubular carbon fiber braid 430 is split into two smaller segments and then split again to form four parallel tubular segments 414, 416, 418 and 420. Mounted within segments 414, 416, 418 and 420 are silicone rubber or other plastic core members. The tubular carbon fiber braid may be backfilled with silicone rubber in other areas, in order to prevent tissue ingrowth into the braid in the areas of the bifurcations. The large diameter braid 430 is covered with an insulative sheath 422, extending to the proximal end of the lead, at which point an electrical connector is mounted to braid 430. As illustrated, the carbon fiber electrode structure is mounted to a flexible, insulative backing member 410, which may be provided with grooves corresponding to the desired configuration of the carbon fiber electrode. As in the embodiments illustrated in FIGS. 1 and 2, the carbon fiber electrode may be retained within the grooves by means of silicone rubber medical adhesive. Alternatively, the backing member 410 may be dispensed with, and the electrode used without a backing member, either subcutaneously or epicardially in a manner analogous to the electrode illustrated in FIG. 3.

The carbon fibers employed to make the tubular braided structures illustrated in the present application are carbon fibers provided with a nickel coating of approximately 0.05–1.5 microns in thickness. This material is commercially available from Chemetronics Research, located in White Plains, N.Y., which can weave the fibers into various textile configurations on request. The individual fibers are aggregated into bundles and the bundles thereafter are woven into a hollow, tubular braid having a inner diameter of approximately 1–5 mm.

Preferably, the fibers are provided with a coating of platinum, iridium, gold or other biocompatible low resistivity metal. The coating may be applied to individual fibers or to the fiber braid using sputtering techniques. Alternatively, the nickel plated fibers may be provided with a gold overcoating using standard electrodeless deposition processes.

The above embodiments illustrate a variety of leads which may be fabricated in accordance with the present invention. However, they are intended to be exemplary, rather than limiting with regards to the claims which follow In conjunction with the above application, we claim:
1. A defibrillation lead, comprising:
an elongated insulated conductor; and
a carbon fiber electrode, coupled to said elongated insulated conductor, said carbon fiber electrode comprising one or more tubular braids of carbon fibers, said tubular braids of carbon fibers arranged to define a generally planar large surface area defibrillation electrode, said tubular braids each provided with an inner core of a flexible biocompatable plastic, said elongated, insulated conductor comprising an extension and continuation of one or more of said tubular braids of carbon fibers.
2. A lead according to claim 1, wherein said inner cores comprise members fabricated of insulative plastic.
3. A lead according to claim 2 wherein said lead is further provided with a flexible, insulative electrode pad to which said tubular, braided carbon fibers and said inner cores are mounted.
4. A lead according to claim 1 or claim 2 or claim 3 wherein said carbon fibers comprise carbon fibers each provided with a coating of a conductive metal, overlaid with a coating of a second, biocompatible metal.
5. A defibrillation lead, comprising:
an elongated insulated conductor; and
a carbon fiber electrode, coupled to said elongated insulated conductor, said carbon fiber electrode comprising one or more tubular braids of carbon fibers, said tubular braids of carbon fibers arranged to define a generally planar, large surface area defibrillation electrode, said tubular braids each provided with an inner core of a flexible, biocompatable plastic, said carbon fibers comprising carbon fibers each provided with a coating of a conductive metal, overlaid with a coating of a second, biocompatible metal.

* * * * *